(12) United States Patent
Adams et al.

(10) Patent No.: US 8,367,359 B1
(45) Date of Patent: Feb. 5, 2013

(54) METABOLIC BIOMARKERS FOR DIABETES AND INSULIN RESISTANCE

(75) Inventors: Sean H. Adams, Davis, CA (US); Oliver Fiehn, Davis, CA (US)

(73) Assignees: The United States of America, as represented by the Secretary of Agriculture, Washington, DC (US); The Regents of the University of California, Oakland, CA (US)

( * ) Notice: Subject to any disclaimer, the term of this patent is extended or adjusted under 35 U.S.C. 154(b) by 9 days.

(21) Appl. No.: 12/910,771

(22) Filed: Oct. 22, 2010

Related U.S. Application Data

(60) Provisional application No. 61/254,304, filed on Oct. 23, 2009.

(51) Int. Cl.
*C12Q 1/54* (2006.01)

(52) U.S. Cl. .......................................................... 435/14

(58) Field of Classification Search ..................... 435/14
See application file for complete search history.

(56) References Cited

U.S. PATENT DOCUMENTS

| | | | |
|---|---|---|---|
| 2007/0087448 A1* | 4/2007 | Nelsestuen | 436/173 |
| 2010/0163720 A1* | 7/2010 | Bethan et al. | 250/282 |
| 2011/0124022 A1* | 5/2011 | Nagalla et al. | 435/15 |

OTHER PUBLICATIONS

Kawasaki et al. (Increased Fructose Concentrations in Blood and Urine in patients with Diabetes. Diabetes Care. 2002. 25(2) 353-357).*
Major et al. (A metabonomic analysis of plasma from Zucker rat strains using gas chromatography/mass spectrometry and pattern recognition. Rapid Communications in Mass Spectrometry. 2006. 20: 3295-3302).*
Zlatkis et al. (Profile of Volatile Metabolites in Urine by Gas Chromatography-Mass Spectrometry. 1973. Analytical Chemistry 45(4) 763-767).*
Yi et al. (Plasma fatty acid metabolic profiling and biomarkers of type 2 diabetes mellitus based on GC/MS and PLS-LDA. FEBS Letters 580 (2006) 6837-6845).*

\* cited by examiner

*Primary Examiner* — Karen Cochrane Carlson
*Assistant Examiner* — Natalie Moss
(74) *Attorney, Agent, or Firm* — Howard V. Owens; John D. Fado; Leslie Shaw

(57) ABSTRACT

Disclosed are small molecule metabolites useful as biomarkers for the evaluation and treatment of pre diabetes, diabetes and insulin resistance.

4 Claims, No Drawings

METABOLIC BIOMARKERS FOR DIABETES AND INSULIN RESISTANCE

CROSS REFERENCE TO RELATED APPLICATIONS

This application claims priority under 35 USC §§119 and 120 to U.S. Provisional Application Ser. No. 61/254,304, filed Oct. 22, 2009.

FIELD OF THE INVENTION

The present invention relates to the identification and use of small molecule metabolites that mark insulin resistance, pre-diabetes and diabetes.

SUMMARY OF THE INVENTION

An embodiment of the invention is the identification of small molecule metabolites that mark diabetes, diabetes risk, insulin resistance, or other metabolic disorders associated with changes in insulin activity as discovered in an analysis of metabolite patterns in plasma samples derived from type 2 diabetic (T2D) human subjects.

Another embodiment of the invention is the combination of newly identified small molecule metabolites with known metabolites to mark metabolic perturbation, diabetes risk, insulin resistance, or other metabolic disorders associated with changes in insulin activity.

Another embodiment of the invention is the use of small molecule metabolites associated with T2D as biomarkers in clinical tests of animal biofluids as a prognostic or diagnostic indicator of diabetes, insulin resistance, or other metabolic disorders associated with changes in insulin activity.

A further embodiment is the use of small molecule metabolites to evaluate responses to pharmacologic, nutritional, or other modalities designed to combat metabolic diseases involving insulin resistance and poor blood sugar control, including, e.g., diabetes, diabetes risk level, insulin resistance, or other metabolic disorders associated with changes in insulin activity.

DEFINITIONS

As used herein:

"MS" refers to Mass Spectrometry.

"Biomarker" refers to small molecule metabolites that mark diabetic, pre diabetic, insulin resistance or other conditions associated with poor blood sugar control or altered insulin activity.

"Treatment" refers to both therapeutic treatment and prophylactic or preventative measures, wherein the object is to reverse, prevent or slow down (lessen) the targeted pathologic condition or disorder. Those in need of treatment include those already with the disorder as well as those prone to have the disorder or those in whom the disorder is to be prevented.

A "pharmaceutically acceptable carrier" includes any and all solvents, dispersion media, coatings, antibacterial and antifungal agents, isotonic and absorption delaying agents, and the like, compatible with pharmaceutical administration (Gennaro, 2000). Preferred examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

The term "subject" as used herein relates to animals, preferably to mammals such as mice, rats, sheep, dogs, cats, horses, monkeys, or cows and, also preferably, to humans.

The term "comparing" refers to assessing whether the results of the determination described herein in detail, i.e. the results of the qualitative or quantitative determination of the at least one metabolite, are identical or similar to reference results or differ there from.

DETAILED DESCRIPTION OF THE INVENTION

Abnormal long-chain fatty acid (LCFA) combustion in skeletal muscle is associated with insulin resistance, but specific signaling moieties that link LCFA β-oxidation to insulin signaling remain controversial. No clinically-relevant biomarkers are available that specifically reflect muscle LCFA catabolism, but these would be useful for T2DM risk assessment, diagnostics, and to understand disease etiology. Use of metabolomic approaches to identify plasma metabolites specifically or robustly altered by changes in muscle LCFA β-oxidation forms provides assessment of the clinically relevant biomarkers disclosed herein. Furthermore, comprehensive analysis of the plasma metabolite profile comparing type 2 diabetics vs. non-diabetics has revealed unique signatures of metabolites that are altered under this condition, and that track blood sugar control markers.

An embodiment of the invention is the identification of biomarkers that are associated with T2D in clinical tests of samples of human or animal biofluids, including but not limited to plasma, serum and urine. Wherein these biomarkers serve as prognostic or diagnostic indicators of pre-diabetes, diabetes, insulin resistance metabolic disorders associated with changes in insulin activity.

A further embodiment of the invention is the use of small molecule metabolites that mark diabetes as discovered in an analysis of metabolite patterns in plasma samples derived from type 2 diabetics (T2D) using MS analysis. The increase or decrease in the concentration of select biomarkers in T2D subjects compared to non diabetic control subjects matched for body mass and other characteristics can be used to mark T2D. Correlation to T2D may be based on single biomarkers or a group/subset of a group of biomarkers.

An additional embodiment of the invention includes clinical tests useful to treat or prevent disease by evaluating biomarker concentration in response to pharmacologic, nutritional, or other interventions that are designed to combat metabolic diseases involving insulin resistance and conditions associated with poor blood sugar control. More particularly, biomarkers elucidated via methodologies of the instant invention find utility related to broad areas of disease therapeutics. Such therapeutic avenues include, but are not limited to:

1) utilisation and recognition of said biomarkers, variants or moieties thereof as direct therapeutic modalities, either alone or in conjunction with an effective amount of a pharmaceutically effective carrier; 2) validation of therapeutic modalities or disease preventative agents as a function of biomarker presence or concentration; 4) use of biomarkers or moieties thereof as a means of elucidating therapeutically viable agents, and 5) synthesis of molecular structures related to said biomarkers, moieties or variants thereof which are constructed and arranged to therapeutically intervene in the disease process.

The metabolites are small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, production and R-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including eg. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Small molecule metabolites of the invention are found in Table 1.

In a further preferred embodiment of the method of the present invention, said at least one metabolite or metabolites is selected from the group delineated as different in T2D vs. non-diabetic subjects in Table 1, including but not exclusive: Metabolite 206604, 223513, 228939, 225539, 226851, 210286, 199794, 228143, oleic acid, 199777, 241310, 270003, 213143, 208655, 212208, 227352, 226853, 281329, 213193, gluconic acid, 223505, 228315, fructose, 222049, 228147, palmitoleic acid, 228911, 281216, 3,6-anhydrogalactose, 281257, 225555, 231713, 213304, glucuronic acid, 227367, 236890, heptadecanoic acid, inulobiose, leucine, 223402, 281229, 2-hydroxybutanoic acid, 223506. Other metabolites altered in diabetes and/or that track blood sugar control indices include, as examples, down-regulated metabolites in the plasma of T2D (Table 1).

Each of said metabolites is a suitable biomarker by its own for the diseases referred to herein. However, most preferably, a group of biomarkers including biomarkers of one of the aforementioned groups is to be determined by the method of the present invention. A group of biomarkers consists, preferably, of at least two, at least three, at least four and, preferably, up to all of the aforementioned biomarkers. Further, it has been found in accordance with the studies underlying the present invention that the aforementioned group of metabolites is particularly well suited as biomarkers for diabetes, insulin resistance, poor blood sugar control or predisposition thereof in female subjects. Accordingly, more preferably, the subject referred to in connection with the aforementioned preferred embodiment is a female.

Metabolites lacking full structural identification ("unknowns") are unambiguously described by BinBase (BB) numbers and full mass spectra, quantifier ions and retention indices. These data are publically available and queryable against all 24,000 samples in BinBase. In the absence of specific nomenclature identification of the biomarker against known chemical standards, identification and concentration of the unnamed biomarker may be accomplished via analysis of the abundance of the relevant MS peak signatures.

A pharmaceutical composition of the agonist or antagonist is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

GC-TOF MS was used to compare the plasma metabolome (254 unique small molecules) of overnight-fasted obese African-American women with or without an uncoupling protein 3 (UCP3) g/a polymorphism (n=28/genotype), and to also determine if metabolites differed between non-diabetic (n=12; 6 each genotype) and T2DM (n=44; 22 each genotype) subjects. Preliminary analysis revealed 23 metabolites increased significantly by $\geq$2-fold (p<0.05) in T2DM. As expected, plasma glucose, LCFAs, and $\beta$-hydroxybutyrate were significantly increased in T2DM, and the plasma branch-chain amino acid leucine was increased by 47% (p$\leq$0.01). T2DM plasma fructose was ~200% of non-diabetics, suggestive of increased endogenous fructose generation. Interestingly, 83% of the molecules elevated in T2DM represent unique, unidentified T2DM-associated factors. Only 2 plasma molecules were reduced significantly by $\geq$50% in T2DM. Multivariate and correlation statistics have been employed to understand if these altered metabolites, in combination with our previously-published data on acylcarnitine patterns in these subjects (Adams et al., J. Nutr., 2009), yield a "metabolic signature" that segregates/clusters type 2 diabetics or that is predictive of persons with disrupted muscle LCFA catabolism. This toolset may be useful to predict T2DM risk, to track efficacy of modalities to thwart T2DM, and to understand the basic biology underlying T2DM and UCP3 function.

The aforementioned samples are, preferably, pretreated before they are used for the method of the present invention. As described in more detail below, said pre-treatment may include treatments required to release or separate the compounds or to remove excessive material or waste. Suitable techniques comprise centrifugation, extraction, fractioning, purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pretreatments depend on the means used for carrying out the method of the invention and are well known to the person skilled in the art.

Pre-treated samples as described before are also comprised by the term "sample" as used in accordance with the present invention.

Moreover, the at least one metabolite can also be determined by a specific chemical or biological assay. Said assay shall comprise means which allow to specifically detect the at least one metabolite in the sample. Preferably, said means are capable of specifically recognizing the chemical structure of the metabolite or are capable of specifically identifying the metabolite based on its capability to react with other compounds or its capability to elicit a response in a biological read out system (e.g., induction of a reporter gene). Means which are capable of specifically recognizing the chemical structure of a metabolite are, preferably, antibodies or other proteins which specifically interact with chemical structures, such as receptors or enzymes. Specific antibodies, for instance, may be obtained using the metabolite as antigen by methods well known in the art. Antibodies as referred to herein include both polyclonal and monoclonal antibodies, as well as fragments thereof, such as Fv, Fab and F(ab)2 fragments that are capable of binding the antigen or hapten.

The term "reference" refers to results, i.e. data of characteristic features of the at least one metabolite, which can be correlated to diabetes, insulin resistance, poor blood sugar control, pre diabetes or a predisposition there for. Such reference results are, preferably, obtained from a sample from a subject known to suffer from diabetes or a subject known to have predisposition therefor. The reference results may be obtained by applying the method of the present invention. Alternatively, but nevertheless also preferred, the reference results may be obtained from sample of a subject known not to suffer from diabetes or a subject known not to have a predisposition therefore, i.e. a healthy subject with respect to diabetes and, more preferably, other diseases as well. More over, the reference, also preferably, could be a calculated reference, most preferably the average or median, for the relative or absolute amount of a metabolite of a population of individuals comprising the subject to be investigated. The absolute or relative amounts of the metabolites of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 or 10,000 subjects. It is to be understood that the subject to be diagnosed by the method of the present invention and the subjects of the said plurality of subjects are of the same species.

More preferably, the reference results, i.e. values for at least one characteristic features of the at least one metabolite, will be stored in a suitable data storage medium such as a database and are, thus, also available for future diagnoses. This also allows efficiently diagnosing predisposition for a disease because suitable reference results can be identified in the database once it has been confirmed (in the future) that the subject from which the corresponding reference sample was obtained (indeed) developed diabetes.

As described above, in a preferred embodiment of the method of the present invention, said determining of the at least one metabolite comprises mass spectrometry (MS). Mass spectrometry as used herein encompasses all techniques which allow for the determination of the molecular weight (i.e. the mass) or a mass variable corresponding to a compound, i.e. a metabolite, to be determined in accordance with the present invention. Preferably, mass spectrometry as used herein relates to GC-MS, LC-MS, direct infusion mass spectrometry, FT-ICR-MS, CE-MS, HPLC-MS, quadrupole mass spectrometry, any sequentially coupled mass spectrometry such as MS-MS or MS-MS-MS, ICP-MS, Py-MS, TOF or any combined approaches using the aforementioned techniques. How to apply these techniques is well known to the person skilled in the art. Moreover, suitable devices are commercially available. More preferably, mass spectrometry as used herein relates to LC-MS and/or GC-MS, i.e. to mass spectrometry being operatively linked to a prior chromatographic separation step. More preferably, mass spectrometry as used herein encompasses quadrupole MS. Most preferably, said quadrupole MS is carried out as follows: a) selection of a mass/charge quotient (m/z) of an ion created by ionisation in a first analytical quadrupole of the mass spectrometer, b) fragmentation of the ion selected in step a) by applying an acceleration voltage in an additional subsequent quadrupole which is filled with a collision gas and acts as a collision chamber, selection of a mass/charge quotient of an ion created by the fragmentation process in step b) in an additional subsequent quadrupole, whereby steps a) to c) of the method are carried out at least once and analysis of the mass/charge quotient of all the ions present in the mixture of substances as a result of the ionisation process, whereby the quadrupole is filled with collision gas but no acceleration voltage is applied during the analysis.

More preferably, said mass spectrometry is liquid chromatography (LC) MS and/or gas chromatography (GC) MS.

Materials & Methods

Subject Group

A detailed description of the human cohorts used in the analysis of metabolite differences between non-diabetics and type 2 diabetics may be found in Adams et al. (J. Nutrition, 139: 1073-1081, 2009). Briefly: Archived plasma samples derived from BMI- and age-matched overweight to obese type 2 diabetic (n=44) and non-diabetic (n=12) Gullah-speaking African-American women with or without a UCP3 g/a missense polymorphism were evaluated (subject characteristics are given in Table 1). Volunteers were recruited as part of the Project Sugar Study described in detail elsewhere (McLean, D. C. et al., American Journal of Physiol. Anthropology 127: 427-38, 2005; Sale, M. M. et al., Diabetes, 2008). Considering that this subject population is of a single sex, displays extraordinarly low genetic admixture, lives in a relatively small geographical space, and has a common dietary intake pattern, we anticipate that this group is well-suited for metabolomics studies since biological signal-to-noise should be low in terms of metabolite signatures. Studies were approved by the Institutional Review Boards of the Medical University of South Carolina, University of Alabama at Birmingham, and the University of California, Davis, and all subjects provided informed consent. Blood was obtained between ~08:00-09:00 by arm venipuncture into EDTA-treated collection tubes after an overnight fast (no food or drink since 20:00 the night before). Plasma was frozen at −20° C. for 1-7 days before transport to −80° C. freezers for longer-term storage. Subjects were instructed to avoid any unusual activity and intentional exercise in the 3 days leading up to the study, and were instructed to continue to eat their habitual diet without unusual deviations. Patients with diabetes did not take doses of oral agents on the evening before and on the morning of study. Patients treated with insulin could take regular or rapid acting insulin at dinner the night before the study but were instructed to withhold any intermediate- or long-acting insulin on the evening before, and to avoid insulin injections on the morning of the study.

Analytical Methods

Plasma Extraction: For preparing the extraction mixture, degassing devices (such as vacuum/ultrasonic bath, or pure argon or nitrogen gas bombs) and a liquid cooling system must be available. A freshly prepared, chilled (−15° C.) and degassed mixture of acetone and isopropanol is prepared at a ratio of 2:1 (v/v). For each solvent, the highest quality (e.g. >99% ultra-pure HPLC-MS gradient grade purity) is used and stored at room temperature in the dark. A pH measurement device ensured neutrality of solvents. Volumes are measured using calibrated pipettes whose accuracies are subjected to quality control routines at least once every six months. An ice bath and liquid nitrogen dewars are used for temporarily storing samples during the process. Large twisters are useful to operate in nitrogen dewars. Extraction is performed in a micro centrifuge tube shaker.

Derivatisation:

A speed vacuum concentrator or lyophiliser is used for drying extracts to complete dryness. A mixture of 40 mg/mL of methoxyamine. HCl in pyridine (p.a. quality) is freshly prepared using an ultrasonicator. In case ATAS (NL) liners are used, pyridine must be exchanged against dimethylformamide as polar, aprotic and basic solvent. N-methyl-N-trimethylsilyltrifluoroacetamide (MSTFA) is used from freshly opened 1-mL bottles. Reagents and solvents are stored in a desiccator in the dark. Derivatizations are carried out in thermoshakers that are set to 45° C. and 37° C. for the first and second reaction step, resp.

Mass Spectrometric Analysis:

GC-MS analysis is carried out on a quadrupole or a time-of-flight mass spectrometer equipped with autosampler and electron impact ionization. Samples are injected in randomized order or appropriate block designs. For each injection sequence, the analysis of quality control samples is a prerequisite (e.g. reagent blanks, method blanks, reference compound mixture, reference design sample). Low bleeding injector septa or septum free injector systems are prerequisite. Standard 10 µL gas chromatography injection needles are mounted into the autosampler. Chromatography is carried out on a 30 m long, 0.32 mm I.D. and 0.25 µm (35%-Phenyl)-methylpolysiloxane column. The GC oven must be temperature programmable up to 360° C. The mass spectrometer must be capable of a data acquisition rate of at least 20 s$^{-1}$ and a mass range of at least 83-500 Da. Raw GC-MS data files are transferred to servers. Long-term data safety is ensured by back up routines on DVDs or by mirrored server space. Data analysis is carried out on office personal computers using the vendor's GC-TOF software that is able to carry out multi-target analysis, including compound identity checks based on mass spectral and retention index matching (e.g. ChromaTOF 2.25). The software must be capable of quantitation by area and height on user defined ion traces.

Brief Summary of Typical Protocol:

Protein Precipitation and Metabolite Extraction

1. Take out 30 µl sample aliquots one by one and add internal standards, e.g. U-$^{13}$C-Sorbitol (200 ng per vial) for normalization, vortex for 10 s.

2. Add 0.4 mL of cold extraction solvent mixture (−15° C., degassed) to each and vortex vigorously for 20 s.

3. Shake the samples in batches of 10 for 5 min in a 4° C. room. When taking out the samples, place them in an ice bath.

4. Centrifuge samples at 20,800 rcf for 2 min.

5. Collect the liquid supernatant of each sample and store in a clean micro centrifuge tubes. The metal balls can be re-used after cleaning. The cell debris pellet can be discarded.

6. Repeat steps 1-5 until all samples are extracted.

7. For storage, extracts must be degassed with a gentle stream of nitrogen or argon gas for 1 min prior to tube closure. Tubes can then be stored in the dark at −80° C. for about four weeks.

8. Dry the extracts in a speed vacuum concentrator or a lyophilizer to complete dryness.

9. For storage, deoxygenate samples with a gentle stream of nitrogen or argon gas for 1 min before closing the tubes. Tubes can then be stored in the dark at −80° C. for at least four weeks.

Derivatization

1. Take out dried samples from store and allow them to warm up to room temperature for at least 15 min before start of derivatization.

2. Add 10 µL of methoxyamine solution (40 mg/mL in dimethylformamide) to each dried extract, and immediately close tubes afterwards.

3. Shake extracts for 90 min at 28° C.

4. Add 180 µL silylating agent (MSTFA) to each tube, and immediately close tubes afterwards.

5. Shake samples for 30 min at 37° C.

6. Transfer sample reaction solutions to glass vials suitable for the GC-MS autosampler. Immediately close each sample with crimps that contain a teflon rubber seal. Wait two hours before injecting the first sample into the GC-MS.

Data Acquisition by GC-MS

1. The mass spectrometer must be tuned according to the manufacturer's manuals for optimal parameters for ion lenses, detector voltage and other settings. Usually, this can be performed in autotune operation.

2. Change or clean the liner every sample, otherwise data for lipids and aromatic compounds will not be reliable.

3. Check that manufacturere's recommended maintenance routines have all been carried out.

4. Inject 1 µL (1.5 µL for ATAS liners) of each sample in splitless, depending on the metabolite concentrations and eventual signal-to-noise ratios in the GC-MS profiles. Injection temperature is set to 230° C. Injection programs have to include syringe washing steps before and after the injection, a sample pumping step for removal of small air bubbles and an air buffer for complete sample removal during injection.

5. Separate metabolites using a GC temperature ramping program. Reasonable values are: GC start conditions at 80° C., 2 min isothermal, ramp with 5° C./min up to 330° C., 5 min isothermal, cool down to initial conditions. The ion source should be turned off during the solvent delay.

6. Detect metabolites by setting the ion source filament energy to 70 eV. Scan a mass range of at least 83-500 Da, or 40-500 Da, if low mass-to-charge (m/z) fragment ions are to be recorded. At least two scans per second should be recorded in full scan mode.

7. Transfer raw GC-MS profile chromatograms to a server station.

Data Analysis

1. For raw data processing, use appropriate software. First choice is the GC-MS manufacturer's software. For general quadrupole mass spectrometers, data deconvolution by the freely available software AMDIS is recommended.

TABLE 1

Identities of plasma metabolites with concentration differences in the plasma of adult women with type 2 diabetes mellitus (n = 44) compared to age- and weight-matched adult women without diabetes (n = 12). Shown are those metabolites that were 150% or 75% of non-diabetic control values, or that were significantly different at $p < 0.1$ (unpaired Student's t-test).*

| Metabolite | Absolute Concentration Difference in type 2 Diabetics vs. non-diabetics (peak area) | | Diabetic, % of Non-Diabetic |
|---|---|---|---|
| 206604 | 1203158 | 0.004492 | 2107.4 |
| 3-hydroxybutanoic acid (β-hydroxybutyrate ketone body) | 36034 | 0.048683 | 437.5 |
| 228939 | 184317 | 0.541997 | 351.3 |
| 223513 | 7951 | 8.49E-07 | 318.8 |
| 225539 | 903 | 6.92E-06 | 305.4 |
| 226851 | 4383 | 2.72E-07 | 294.0 |
| 210286 | 7365 | 2.59E-06 | 281.7 |
| 199794 | 43640 | 1.53E-07 | 280.5 |
| 228143 | 1639 | 4.74E-05 | 270.6 |
| oleic acid | 14430 | 0.00105 | 263.3 |
| 199777 | 170571 | 1.69E-09 | 249.4 |
| 241310 | 915 | 1.12E-06 | 247.5 |
| 270003 | 3498 | 1.94E-06 | 244.1 |
| 204465 | 3537 | 0.550693 | 236.6 |
| 213143 | 1420 | 9.94E-10 | 229.8 |
| 212208 | 4904 | 0.000607 | 218.1 |
| 208655 | 2276 | 4.96E-05 | 216.4 |
| 227352 | 1826 | 3.55E-07 | 212.8 |
| 226853 | 1271 | 0.002346 | 210.8 |
| 228315 | 2274 | 0.464227 | 210.4 |
| 213193 | 667 | 3.51E-08 | 207.1 |
| 281329 | 691 | 0.001038 | 206.2 |
| gluconic acid | 2724 | 1.33E-07 | 206.0 |
| 223505 | 2022 | 1.66E-05 | 202.6 |
| fructose | 257992 | 3.43E-08 | 201.2 |
| 222049 | 4723 | 0.001433 | 200.3 |
| 228147 | 415 | 1.88E-06 | 187.1 |
| palmitoleic acid | 5092 | 0.016313 | 181.0 |
| 281216 | 2151 | 0.032345 | 179.9 |
| 228911 | 20101 | 0.000579 | 178.6 |
| 231713 | 217 | 0.00199 | 175.1 |
| 3,6-anhydrogalactose | 1246 | 1.92E-06 | 175.0 |
| 281257 | 2974 | 1.83E-06 | 172.8 |
| 225555 | 3249 | 0.114927 | 172.6 |
| 213304 | 772 | 0.00012 | 167.6 |
| glucuronic acid | 1106 | 0.03242 | 164.4 |
| 227367 | 251 | 0.001415 | 163.6 |
| sucrose | 589 | 0.505118 | 156.8 |
| glucose | 596395 | 5.14E-06 | 156.4 |
| 281229 | 596 | 0.05042 | 155.9 |
| 236890 | 9571 | 0.106175 | 154.4 |
| heptadecanoic acid | 6274 | 0.038575 | 153.9 |
| inulobiose 2 | 529 | 0.005449 | 152.4 |
| leucine | 52273 | 0.011352 | 147.4 |
| 223402 | 51982 | 0.011212 | 147.3 |
| 2-hydroxybutanoic acid | 45283 | 0.040355 | 145.0 |
| 223506 | 1663 | 0.004005 | 140.7 |
| 274531 | 662 | 0.090695 | 136.4 |
| 2-deoxyerythritol | 2703 | 0.001577 | 132.7 |
| linoleic acid | 2113 | 0.092294 | 131.9 |
| palmitic acid | 23477 | 0.04879 | 131.2 |
| phosphoethanolamine | 515 | 0.067484 | 131.0 |
| uridine | 254 | 0.02067 | 129.9 |
| 2-ketoisocaproic acid | 1306 | 0.045047 | 127.1 |
| 226935 | 7606 | 0.04324 | 126.7 |
| xylose | 1139 | 0.014629 | 126.0 |
| cystine | 7558 | 0.061529 | 124.8 |
| histidine | 10558 | 0.01981 | 123.5 |
| 217797 | 1411 | 0.015875 | 121.2 |
| serine | 18981 | 0.070326 | 120.9 |
| Total branched-chain amino acids (BCAAs) + metabolites (valine, leucine, isoleucine, ketoisocaproic acid) | 117028 | 0.057367 | 120.2 |
| Total BCAA (valine, leucine, isoleucine) | 115722 | 0.058833 | 120.1 |
| stearic acid | 119485 | 0.018492 | 120.0 |
| 220169 | -3029 | 0.083012 | 86.2 |
| tyrosine | -27674 | 0.046953 | 85.8 |
| 213733 | -509 | 0.040706 | 82.8 |
| lysine | -31386 | 0.031029 | 81.6 |
| 226841 | -4797 | 0.047908 | 80.8 |
| 200427 | -9056 | 0.018543 | 80.5 |
| 204425 | -2887 | 0.002215 | 79.4 |
| 213526 | -4401 | 0.000825 | 78.3 |
| ethanolamine | -105773 | 0.020283 | 78.0 |
| 200429 | -8024 | 0.021525 | 77.8 |
| 215682 | -8589 | 0.013975 | 77.3 |
| 221431 | -4106 | 0.014618 | 77.2 |
| 213961 | -3643 | 0.040719 | 76.3 |
| 229105 | -6652 | 0.061982 | 74.8 |
| 224033 | -2089 | 0.147945 | 74.7 |
| 226864 | -854 | 0.090138 | 74.3 |
| 226849 | -3029 | 0.155581 | 74.1 |
| 226916 | -2997 | 0.305944 | 74.1 |
| 240018 | -559 | 0.11936 | 73.8 |
| arachidonic acid | -9346 | 0.006359 | 73.4 |
| 220010 | -3402 | 0.003713 | 72.8 |
| glycine | -90613 | 0.019996 | 72.2 |
| 223548 | -643 | 0.004802 | 72.0 |
| 223973 | -1903 | 0.025398 | 71.9 |
| 240264 | -726 | 0.069733 | 71.9 |
| 235373 | -2979 | 0.212995 | 71.8 |
| 227358 | -2761 | 0.130707 | 71.8 |
| 202572 | -2274 | 0.497109 | 71.5 |
| 226859 | -8115 | 0.192243 | 70.4 |
| 223576 | -1716 | 0.161669 | 69.5 |
| glycerol-alpha-phosphate | -7358 | 0.002141 | 69.2 |
| 226911 | -2525 | 0.109537 | 68.5 |
| putrescine | -1843 | 0.242229 | 67.8 |
| 281193 | -1104 | 0.110333 | 67.6 |
| 217870 | -19766 | 0.055383 | 66.6 |
| 226923 | -1900 | 0.060475 | 66.4 |
| 231161 | -209 | 1.46E-05 | 65.5 |
| 213697 | -626 | 0.044689 | 65.1 |
| 240017 | -579 | 0.028334 | 64.5 |
| 223527 | -2093 | 0.0505 | 64.3 |
| 281132 | -559 | 8.21E-05 | 60.2 |
| 270508 | -1394 | 0.000188 | 59.2 |
| lactic acid | -402727 | 0.034438 | 46.2 |
| 281134 | -1983 | 5.59E-07 | 45.8 |
| 241403 | -5610 | 0.034246 | 25.0 |

*Metabolites with numerical identities only are unnamed metabolites; numbers refer to the arbitrary nomenclature derived from the laboratory of Oliver Fiehn (Univ. of CA, Davis: http://eros.fiehnlab.ucdavis.edu:8080/binbase-compound/).

TABLE 2

Plasma metabolites with significantly-altered concentrations in non-diabetic obese African-American women harboring a UCP3 g/a missense allele.

| | g/g genotype (n = 6) | g/a genotype (n = 6) | Relevant Metabolic Pathway | g/a to g/g Ratio |
|---|---|---|---|---|
| Increased in non-diabetic g/a: | | | | |
| BB226860 | 2552 ± 669 | 5851 ± 1302 | unknown | 2.29* |
| BB219174 | 6966 ± 988 | 10253 ± 1074 | unknown | 1.47* |
| Decreased in non-diabetic g/g: | | | | |
| BB223521 | 3569 ± 340 | 2516 ± 318 | unknown | 0.71* |
| phosphoric acid | 1540725 ± 106083 | 1065028 ± 88171 | acid/base balance? | 0.69** |
| BB223506 | 4884 ± 343 | 3288 ± 483 | unknown | 0.67* |
| BB281189 | 432579 ± 45901 | 285112 ± 14032 | unknown | 0.66* |
| inulobiose | 1223 ± 152 | 795 ± 87 | carbohydrate | 0.65* |
| BB228147 | 579 ± 67 | 374 ± 49 | unknown | 0.65* |
| BB211382 | 36484 ± 3617 | 21651 ± 3493 | unknown | 0.59** |
| cysteine | 24519 ± 4380 | 13827 ± 1928 | amino acid | 0.56* |
| 2-oxoglutarate (α-ketoglutarate) | 2209 ± 240 | 1182 ± 130 | TCA cycle/transamination | 0.54** |
| BB281112 | 18342 ± 2886 | 9189 ± 2265 | unknown | 0.50* |
| BB228144 | 3874 ± 659 | 1910 ± 524 | unknown | 0.49* |
| BB239966 | 2358 ± 418 | 1158 ± 308 | unknown | 0.49* |
| glutamic acid (glutamate) | 48146 ± 7473 | 21048 ± 1427 | amino acid | 0.44** |
| BB222169 | 25526 ± 4397 | 10743 ± 4133 | unknown | 0.42* |

‡Values are quantifier peak height means SEM; see Supplemental Materials for full list of metabolites including those whose concentration differences were not statistically significant;
*p ≤ 0.05;
**p ≤ 0.01

TABLE 3

Identifiable plasma metabolites with significantly-altered concentrations in obese non-diabetic vs. type 2 diabetic African-American women.

| | Non-Diabetic (n = 12) | Diabetic (n = 43) | Relevant Metabolic Pathway | Diabetic/Non-Diabetic Ratio |
|---|---|---|---|---|
| Increased in Diabetes: | | | | |
| 3-hydroxybutanoic acid (β-hydroxybutyrate) | 10676 ± 1455 | 47424 ± 9450 | lipid/fatty acid | 4.44* |
| oleic acid | 8837 ± 1105 | 23377 ± 2189 | lipid/fatty acid | 2.65*** |
| gluconic acid | 2570 ± 230 | 5317 ± 229 | carbohydrate | 2.07**** |
| fructose | 255053 ± 34001 | 517922 ± 18549 | carbohydrate | 2.03**** |
| palmitoleic acid | 6286 ± 1444 | 11400 ± 1018 | lipid/fatty acid | 1.81* |
| 3,6-anhydrogalactose | 1660 ± 147 | 2920 ± 116 | carbohydrate | 1.76**** |
| glucuronic acid | 1718 ± 151 | 2844 ± 264 | carbohydrate | 1.66* |
| glucose | 1057532 ± 90953 | 1644213 ± 56650 | carbohydrate | 1.56**** |
| heptadecanoic acid | 11630 ± 554 | 17911 ± 1564 | lipid/fatty acid | 1.54* |
| inulobiose | 1009 ± 106 | 1546 ± 92 | carbohydrate | 1.53** |
| leucine | 110271 ± 14147 | 164281 ± 9806 | amino acid | 1.49** |
| 2-hydroxybutanoic acid (α-hydroxybutyrate) | 100560 ± 21376 | 146853 ± 9844 | amino acid | 1.46* |
| 2-deoxyerythritol | 8270 ± 727 | 10950 ± 383 | lipid/fatty alcohol | 1.32** |
| palmitic acid | 75185 ± 5308 | 98294 ± 6003 | lipid/fatty acid | 1.31* |
| 2-ketoisocaproic acid (α-ketoisocaproate) | 4809 ± 462 | 6169 ± 309 | amino acid | 1.28* |
| uridine | 850 ± 51 | 1085 ± 51 | pyrimidine | 1.28* |
| cystine | 30534 ± 3583 | 38496 ± 1818 | amino acid | 1.26* |
| xylose | 4388 ± 290 | 5479 ± 221 | carbohydrate/pentose phosphate | 1.25* |
| histidine | 44969 ± 2332 | 56071 ± 2178 | amino acid | 1.25** |
| stearic acid | 598153 ± 31201 | 719217 ± 24664 | lipid/fatty acid | 1.20* |
| Decreased in Diabetes: | | | | |
| benzylalcohol | 17762 ± 1062 | 15741 ± 405 | phenolic metabolite or | 0.89* |
| benzoic acid | 37841 ± 2445 | 32968 ± 1066 | phenolic metabolite or | 0.88* |
| lysine | 170439 ± 13635 | 141626 ± 6008 | amino acid | 0.83* |
| ethanolamine | 479789 ± 42252 | 380214 ± 19511 | choline precursor | 0.79* |
| arachidonic acid | 35123 ± 3669 | 26058 ± 1410 | lipid/fatty acid | 0.74** |
| glycine | 326074 ± 41720 | 239650 ± 16035 | amino acid | 0.74* |
| glycerol-3-phosphate (glycerol-α-phosphate) | 23920 ± 2430 | 16571 ± 1018 | glycerophospholipid | 0.69** |

‡Values are quantifier peak height means ± SEM; see Supplemental Materials for information on unknown metabolites significantly changed in T2DM;
*p ≤ 0.05;
**p ≤ 0.01;
***p ≤ 0.001;
****p ≤ 0.0001, (unpaired t-test)

TABLE 4

Metabolite (BB) & Ret index.

| BB name | ret index | quant ion |
|---|---|---|
| 206604 | 653437 | 147 |
| 3-hydroxybutanoic acid | 278929 | 191 |
| 223513 | 808133 | 98 |
| 228939 | 253563 | 154 |
| 225539 | 798935 | 387 |
| 226851 | 788409 | 373 |
| 210286 | 701682 | 217 |
| 199794 | 681176 | 361 |
| maltose | 946608 | 361 |
| 228143 | 673081 | 187 |
| oleic acid | 778858 | 339 |
| 199777 | 675254 | 217 |
| 241310 | 782338 | 373 |
| 270003 | 736904 | 217 |
| 213143 | 873684 | 446 |
| 208655 | 688305 | 217 |

TABLE 4-continued

Metabolite (BB) & Ret index.

| BB name | ret index | quant ion |
|---|---|---|
| 212208 | 705463 | 147 |
| 227352 | 927021 | 132 |
| 226853 | 966330 | 272 |
| 281329 | 705694 | 245 |
| 213193 | 865396 | 446 |
| gluconic acid | 693140 | 333 |
| 223505 | 810335 | 246 |
| 228315 | 553878 | 299 |
| fructose | 642325 | 307 |
| 222049 | 701919 | 117 |
| 228147 | 699907 | 261 |
| palmitoleic acid | 706298 | 129 |
| 228911 | 632392 | 307 |
| 281216 | 605436 | 144 |
| 3,6-anhydrogalactose | 589230 | 231 |
| 281257 | 612012 | 231 |
| 225555 | 685994 | 266 |
| 231713 | 692917 | 244 |
| 213304 | 930533 | 156 |
| glucuronic acid | 666743 | 333 |
| 227367 | 995564 | 217 |
| sucrose | 913309 | 271 |
| 236890 | 628019 | 217 |
| glucose | 657634 | 160 |
| heptadecanoic acid | 750645 | 117 |
| inulobiose 2 | 930708 | 204 |
| leucine | 345953 | 158 |
| 223402 | 345709 | 158 |
| 281229 | 986303 | 310 |
| 2-hydroxybutanoic acid | 258175 | 131 |
| 223506 | 802836 | 246 |
| taurine | 557250 | 326 |
| arachidic acid | 856486 | 117 |
| 224552 | 494599 | 239 |
| 274531 | 706670 | 331 |
| 218761 | 336333 | 116 |
| 2-deoxyerythritol | 422939 | 103 |
| linoleic acid | 777102 | 337 |
| 281143 | 617834 | 328 |
| palmitic acid | 711066 | 313 |
| ornithine | 527822 | 142 |
| 227322 | 364439 | 142 |
| proline | 364232 | 142 |
| 2-ketoisocaproic acid | 310629 | 200 |
| 226935 | 983996 | 310 |
| 2-oxogluconic acid | 542152 | 201 |
| uridine | 856953 | 258 |
| phosphoethanolamine | 604454 | 100 |
| tocopherol gamma | 1026222 | 223 |
| cystine | 804143 | 218 |
| shikimic acid | 607609 | 204 |
| xylose | 542808 | 103 |
| histidine | 663393 | 154 |
| 273236 | 1108221 | 311 |
| serine | 394650 | 204 |
| 204465 | 474367 | 140 |
| 217797 | 655403 | 273 |
| cysteine | 499495 | 220 |
| adipic acid | 475399 | 111 |
| stearic acid | 787358 | 117 |
| valine | 313224 | 144 |
| 239843 | 890991 | 290 |
| myristic acid | 634543 | 285 |
| 226845 | 795371 | 232 |
| alanine | 243537 | 116 |
| 226922 | 696043 | 139 |
| methionine | 483425 | 176 |
| palmitic acid butyl ester | 768467 | 129 |
| aconitic acid | 586574 | 229 |
| lignoceric acid | 977850 | 117 |
| 268506 | 301113 | 216 |
| alpha mannosylglycerate | 633295 | 217 |
| 281131 | 1071318 | 371 |
| 281108 | 857519 | 362 |
| cysteine-glycine | 715639 | 220 |

TABLE 4-continued

Metabolite (BB) & Ret index.

| BB name | ret index | quant ion |
|---|---|---|
| asparagine | 553791 | 116 |
| 273450 | 462401 | 193 |
| 281112 | 802983 | 232 |
| kynurenine | 769271 | 218 |
| 281158 | 500924 | 240 |
| phenylalanine | 538016 | 218 |
| levoglucosan | 569799 | 204 |
| 227364 | 572785 | 314 |
| 239883 | 869427 | 290 |
| 281200 | 816855 | 445 |
| 228144 | 800275 | 290 |
| 228583 | 302763 | 216 |
| 241572 | 1082682 | 299 |
| aspartic acid | 480543 | 232 |
| erythritol | 471274 | 205 |
| N-methylalanine | 286258 | 130 |
| glycolic acid | 229810 | 177 |
| glutamic acid | 527101 | 246 |
| 226850 | 385813 | 183 |
| 228612 | 756779 | 230 |
| 228018 | 563074 | 275 |
| 4-hydroxyproline | 481319 | 140 |
| phosphoric acid | 344674 | 299 |
| 281080 | 944566 | 429 |
| indole-3-acetate | 685195 | 202 |
| uric acid | 731185 | 441 |
| 225403 | 562683 | 243 |
| 226888 | 580679 | 170 |
| 269969 | 410322 | 279 |
| citric acid | 617288 | 273 |
| 281118 | 1037677 | 309 |
| 223495 | 538501 | 170 |
| 223536 | 521629 | 156 |
| 2-hydroxyvaleric acid | 310750 | 131 |
| 226867 | 735540 | 290 |
| behenic acid | 919675 | 117 |
| isothreonic acid | 489846 | 292 |
| creatinine | 502434 | 115 |
| 211382 | 773139 | 147 |
| isoleucine | 356931 | 158 |
| 1-hexadecanol | 679338 | 299 |
| isonicotinic acid | 367074 | 180 |
| 2-aminoadipic acid | 572700 | 260 |
| threonine | 409403 | 117 |
| 281348 | 241383 | 151 |
| glutamine | 600452 | 156 |
| pyrophosphate | 548254 | 451 |
| 269151 | 341172 | 130 |
| inositol myo- | 729867 | 305 |
| 221569 | 425557 | 156 |
| 240439 | 584307 | 170 |
| 221572 | 444313 | 170 |
| 281271 | 711045 | 451 |
| 213353 | 695971 | 293 |
| lathosterol | 1095135 | 255 |
| 281128 | 498007 | 156 |
| 223521 | 1166398 | 283 |
| tryptophan | 779834 | 202 |
| 224788 | 493150 | 228 |
| 224551 | 501237 | 228 |
| 229268 | 407022 | 263 |
| 228401 | 594044 | 170 |
| pseudo uridine | 813829 | 217 |
| glycerol | 343749 | 205 |
| 1-monoolein | 952993 | 129 |
| 229108 | 281476 | 234 |
| 1-monostearin | 959625 | 399 |
| 241369 | 194932 | 172 |
| 224037 | 606591 | 170 |
| 226792 | 716792 | 387 |
| fumaric acid | 390708 | 245 |
| 238566 | 611453 | 170 |
| 239966 | 806614 | 290 |
| indole-3-lactate | 764543 | 202 |
| 235678 | 530661 | 329 |

TABLE 4-continued

Metabolite (BB) & Ret index.

| BB name | ret index | quant ion |
|---|---|---|
| 281120 | 231838 | 97 |
| 228809 | 428316 | 124 |
| tocopherol beta | 1022809 | 222 |
| pelargonic acid | 399163 | 117 |
| citrulline | 620728 | 157 |
| 281186 | 760555 | 315 |
| 234579 | 378003 | 315 |
| 228897 | 379191 | 218 |
| 229073 | 254699 | 228 |
| 226865 | 552707 | 411 |
| 224521 | 352767 | 218 |
| pyrazine 2,5-dihydroxy | 396061 | 241 |
| 281178 | 258298 | 144 |
| 224547 | 538202 | 275 |
| 223597 | 1204498 | 297 |
| mannitol | 665209 | 103 |
| 2-phenylpropanol | 319992 | 193 |
| 269983 | 494553 | 263 |
| 272306 | 253512 | 193 |
| 231657 | 286430 | 187 |
| 281107 | 206299 | 119 |
| 200411 | 595016 | 116 |
| 224849 | 535229 | 275 |
| 239859 | 797156 | 218 |
| lactic acid | 215380 | 191 |
| 281125 | 566380 | 94 |
| urea | 331223 | 171 |
| 226909 | 861795 | 290 |
| 281328 | 278237 | 220 |
| 228927 | 313497 | 165 |
| benzylalcohol | 281322 | 165 |
| 227298 | 374409 | 211 |
| 227353 | 306967 | 218 |
| 201887 | 1200427 | 316 |
| 227743 | 627324 | 156 |
| threonic acid | 497167 | 292 |
| 218520 | 232023 | 147 |
| tocopherol alpha | 1067178 | 237 |
| glyceric acid | 373972 | 189 |
| 211916 | 440480 | 100 |
| 224539 | 566862 | 296 |
| 226855 | 511474 | 270 |
| cholesterol | 1077630 | 129 |
| 217838 | 289054 | 214 |
| 281363 | 710284 | 290 |
| 281185 | 226102 | 95 |
| 228900 | 243069 | 125 |
| 217866 | 237804 | 228 |
| benzoic acid | 338043 | 179 |
| 216428 | 505415 | 223 |
| 281111 | 236617 | 112 |
| arginine + ornithine | 619420 | 142 |
| 281124 | 490965 | 291 |
| 281145 | 216493 | 97 |
| 202599 | 570779 | 173 |
| 219174 | 506055 | 173 |
| 223905 | 257174 | 248 |
| 281119 | 883595 | 359 |
| 268590 | 282017 | 140 |
| 281346 | 429630 | 218 |
| 221574 | 354121 | 85 |
| tyrosine | 671085 | 218 |
| 227365 | 405467 | 114 |
| 226908 | 737073 | 213 |
| 224526 | 334987 | 234 |
| 215490 | 315917 | 130 |
| 242405 | 291859 | 139 |
| lauric acid | 547810 | 117 |
| 226910 | 793299 | 173 |
| 228885 | 250227 | 85 |
| 224522 | 279422 | 174 |
| 281268 | 448141 | 174 |
| 229203 | 840930 | 94 |
| 211898 | 413647 | 270 |
| 225272 | 416106 | 182 |
| 223717 | 477769 | 155 |
| 226848 | 827200 | 202 |
| 239882 | 682727 | 228 |
| 238358 | 640923 | 239 |
| 281133 | 209890 | 120 |
| monopalmitin-1-glyceride | 901207 | 371 |
| 220169 | 304229 | 174 |
| 239873 | 732710 | 391 |
| lysine | 663816 | 156 |
| 223634 | 471218 | 140 |
| 204344 | 246354 | 147 |
| 239593 | 614313 | 269 |
| 223578 | 397473 | 272 |
| 281249 | 692691 | 261 |
| 213733 | 597844 | 271 |
| 226842 | 544485 | 171 |
| 224808 | 458884 | 181 |
| 226846 | 442001 | 258 |
| 227391 | 527630 | 170 |
| alpha ketoglutaric acid | 507734 | 198 |
| 224571 | 371691 | 140 |
| glycerol-beta-phosphate | 574994 | 211 |
| 200427 | 452933 | 154 |
| 229962 | 951858 | 397 |
| 215504 | 512079 | 373 |
| 217842 | 447001 | 265 |
| 281172 | 589910 | 140 |
| 224529 | 549948 | 275 |
| 281106 | 485548 | 232 |
| 239995 | 655244 | 287 |
| 281122 | 234713 | 105 |
| 222058 | 477647 | 366 |
| 219021 | 335520 | 228 |
| 226927 | 824957 | 445 |
| 240265 | 672366 | 139 |
| 226843 | 551430 | 171 |
| 227345 | 395995 | 186 |
| 226841 | 759286 | 232 |
| 281166 | 934476 | 290 |
| 222169 | 975088 | 144 |
| 223500 | 516216 | 269 |
| 199773 | 755246 | 215 |
| 226844 | 641635 | 301 |
| ethanolamine | 342787 | 174 |
| 224792 | 436689 | 155 |
| 204425 | 448206 | 350 |
| 200429 | 438443 | 174 |
| 281147 | 329324 | 106 |
| oxalic acid | 259625 | 147 |
| 281189 | 226160 | 105 |
| 241114 | 425547 | 238 |
| 215682 | 433076 | 174 |
| 239852 | 712000 | 373 |
| conduritol-beta-epoxide | 704220 | 318 |
| 221431 | 427636 | 174 |
| 234491 | 489261 | 226 |
| 281150 | 388815 | 112 |
| 281148 | 783627 | 331 |
| 217867 | 400245 | 154 |
| 223708 | 354552 | 273 |
| 223938 | 492335 | 184 |
| 213526 | 284610 | 201 |
| 226858 | 356536 | 241 |
| 227366 | 283401 | 159 |
| succinic acid | 370518 | 247 |
| 215355 | 338105 | 188 |
| 221562 | 273779 | 98 |
| 228309 | 595001 | 156 |
| 226903 | 833661 | 313 |
| 200624 | 421877 | 373 |
| 223541 | 365519 | 98 |
| 213961 | 897509 | 91 |
| 281109 | 628352 | 98 |
| 223492 | 384421 | 142 |
| 226860 | 690521 | 139 |

TABLE 4-continued

Metabolite (BB) & Ret index.

| BB name | ret index | quant ion |
|---|---|---|
| 210891 | 265181 | 130 |
| 217784 | 431379 | 239 |
| 228203 | 457545 | 152 |
| 226916 | 510239 | 224 |
| 226849 | 541089 | 388 |
| 223499 | 675563 | 285 |
| 224881 | 486165 | 309 |
| 240018 | 904978 | 290 |
| arachidonic acid | 833292 | 91 |
| 229105 | 297744 | 100 |
| 231590 | 321781 | 114 |
| 226864 | 691552 | 211 |
| glycine | 364262 | 174 |
| 223973 | 1028825 | 243 |
| 241403 | 468354 | 212 |
| 224798 | 464635 | 329 |
| 226280 | 369173 | 98 |
| 220010 | 1027429 | 227 |
| 240264 | 455266 | 320 |
| 226859 | 926164 | 290 |
| 224033 | 605457 | 98 |
| 223548 | 749189 | 294 |
| 223778 | 226081 | 159 |
| 235373 | 407853 | 258 |
| 281187 | 574112 | 185 |
| 227358 | 308098 | 142 |
| glycerol-alpha-phosphate | 588999 | 299 |
| 226911 | 914309 | 290 |
| 220009 | 459742 | 172 |
| putrescine | 588249 | 174 |
| 281182 | 518697 | 228 |
| 226923 | 743658 | 290 |
| 281193 | 557891 | 144 |
| 223576 | 467132 | 329 |
| 231161 | 575302 | 362 |
| 223527 | 373284 | 158 |
| 223566 | 624258 | 156 |
| 213697 | 456893 | 232 |
| 217870 | 401556 | 142 |
| 240017 | 351090 | 294 |
| 281132 | 608773 | 276 |
| 270508 | 1084500 | 227 |
| 202572 | 613924 | 217 |
| 281134 | 781899 | 324 |

What is claimed:

1. A method for screening a subject for insulin resistance, diabetes, diabetes risk, pre-diabetes, or diseases involving altered insulin activity comprising:
  a. obtaining a plasma, tissue, or biofluid sample from the subject,
  b. determining relative or absolute abundance of a metabolite or metabolites present in the sample by performing gas chromatogram mass spectrometric analysis on the sample for the presence or absence of metabolites, wherein a scan of the mass range is 40-500 Da,
  c. comparing the peak areas or heights found in the scan to differential peak areas or heights of the metabolites 3 hydroxybutanoic acid, oleic acid, gluconic acid, fructose, palmitoleic acid, (3,6) andhydrogalactose, glucuronic acid, sucrose, glucose, heptadecanoic acid, inulobiose 2, leucine, 2-hydroxybutanoic acid, 2-deoxyerythritol, linoleic acid, palmitic acid, phosphoethanolamine, uridine, 2-ketoisocaproic acid, xylose, cystine, histidine, serine, valine, leucine, isoleucine, stearic acid, tyrosine, lysine, ethanolamine, arachidonic acid, glycerol-alpha-phosphate, putrescine, lactic acid 206604, 228939, 223513, 225539, 226851, 210286, 199794, 228143, 199777, 270003, 241310, 213143, 208655, 212208, 227352, 226853, 281329, 213193, 223505, 228315, 222049, 228147, 228911, 281216, 281257, 225555, 231713, 213304, 227367, 236890, 223402, 281229, 223506 found in subjects with insulin resistance, diabetes or pre-diabetic conditions.

2. The method of claim 1 wherein an enzymatic or colorimetric analysis is used in addition to gas chromatogram to determine relative or absolute abundance of a metabolite or metabolites.

3. A method for assessing therapeutic efficacy of a drug, or pharmacologic, nutritional, or other modalities used to treat or prevent insulin resistance, diabetes, and diseases associated with altered insulin activity conditions in a subject comprising:
  a. administering a drug or therapeutic modality to the subject,
  b. obtaining a plasma, tissue, or other biofluid sample from the subject,
  c. determining the relative or absolute abundance of the metabolites 3 hydroxybutanoic acid, oleic acid, qluconic acid, fructose, palmitoleic acid, (3,6) andhydroqalactose, qlucuronic acid, sucrose, glucose, heptadecanoic acid, inulobiose 2, leucine, 2-hydroxybutanoic acid, 2-deoxyerythritol, linoleic acid, palmitic acid, phosphoethanolamine, uridine, 2-ketoisocaproic acid, xylose, cystine, histidine, serine, valine, leucine, isoleucine, stearic acid, tyrosine, lysine, ethanolamine, arachidonic acid, glycerol-alpha-phosphate, putrescine, lactic acid, 206604, 228939, 223513, 225539, 226851, 210286, 199794, 228143, 199777, 270003, 241310, 213143, 208655, 212208, 227352, 226853, 281329, 213193, 223505, 228315, 222049, 228147, 228911, 281216, 281257, 225555, 231713, 213304, 227367, 236890, 223402, 281229, 223506 by performing gas chromatogram mass spectrometric analysis on the sample for the presence or absence of metabolites, wherein a scan of the mass range is 40-500 Da,
  d. comparing the peak areas or heights found in the scan to differential peak areas or heights of metabolites found in subjects with insulin resistance or diabetic or pre-diabetic conditions wherein a significant increase or decrease in differential peak areas or heights of metabolites associated with insulin resistance, diabetes, or pre-diabetes conditions indicates therapeutic efficacy.

4. The method of claim 3 wherein an enzymatic or colorimetric analysis is used in addition to a gas chromatogram to determine relative or absolute abundance of the metabolites.

* * * * *